United States Patent
Niedzwiecki et al.

(10) Patent No.: US 10,568,866 B1
(45) Date of Patent: Feb. 25, 2020

(54) COMPOSITION AND ITS USE FOR INCREASING INNATE IMMUNE HEALTH

(71) Applicant: Matthias W Rath, Aptos, CA (US)

(72) Inventors: Aleksandra Niedzwiecki, Aptos, CA (US); Matthias W Rath, Aptos, CA (US); Anna Goc, Sanjose, CA (US); Waldemar Sumera, Sanjose, CA (US)

(73) Assignee: Matthias W. Rath, Aptos, CA (US)

( * ) Notice: Subject to any disclaimer, the term of this patent is extended or adjusted under 35 U.S.C. 154(b) by 0 days.

(21) Appl. No.: 16/152,922

(22) Filed: Oct. 5, 2018

(51) Int. Cl.
| | | |
|---|---|---|
| *A61K 31/375* | (2006.01) | |
| *A61K 31/714* | (2006.01) | |
| *A61K 31/355* | (2006.01) | |
| *A61K 36/73* | (2006.01) | |
| *A61K 31/737* | (2006.01) | |
| *A61K 36/9068* | (2006.01) | |
| *A61P 37/00* | (2006.01) | |
| *A61K 33/04* | (2006.01) | |
| *A61K 31/385* | (2006.01) | |
| *A61K 36/605* | (2006.01) | |
| *A61K 36/77* | (2006.01) | |
| *A61K 36/736* | (2006.01) | |
| *A61K 33/30* | (2006.01) | |

(52) U.S. Cl.
CPC .......... *A61K 31/375* (2013.01); *A61K 31/355* (2013.01); *A61K 31/385* (2013.01); *A61K 31/714* (2013.01); *A61K 31/737* (2013.01); *A61K 33/04* (2013.01); *A61K 33/30* (2013.01); *A61K 36/605* (2013.01); *A61K 36/73* (2013.01); *A61K 36/736* (2013.01); *A61K 36/77* (2013.01); *A61K 36/9068* (2013.01); *A61P 37/00* (2018.01)

(58) Field of Classification Search
CPC ...... A61K 31/375; A61K 33/30; A61K 36/77; A61K 36/605; A61K 31/385; A61K 33/04; A61K 36/736; A61K 36/9068; A61K 31/737; A61K 36/73; A61K 31/355; A61K 31/714; A61P 37/00
See application file for complete search history.

(56) References Cited

U.S. PATENT DOCUMENTS

2014/0127179 A1* 5/2014 Thornthwaite ...... A61K 31/716
424/94.1

FOREIGN PATENT DOCUMENTS

| CN | 104886571 | * | 9/2015 | |
| CN | 107006837 | * | 8/2017 | |
| CN | 107019737 | * | 8/2017 | |
| EP | 2260856 A1 | * | 12/2010 | ............. A61K 33/04 |

OTHER PUBLICATIONS

CN104886571A (Year: 2015).*
Eric Vivier et. al. Innate or Adaptive Immunity? The Example of Natural Killer Cells, Science. Jan. 7, 2011; 331 (6013): 44-49.
Martin J. Spiering, Primer on the Immune System, vol. 37, No. 2 Alcohol Research: Current Reviews.

* cited by examiner

*Primary Examiner* — Snigdha Maewall
(74) *Attorney, Agent, or Firm* — Geeta Kadambi; Riddhi IP LLC

(57) ABSTRACT

A composition of natural and chemical nutrients such as Vitamin C, Vitamin B-complex, Vitamin E, *Aronia melanocarpa* extract, Fucoidan, Ginger extract, Zinc, Selenium, Alpha lipoic acid, White mulberry extract, Lychee fruit extract and Sour (Tart) cherry fruit extract are made for mammal consumption in liquid or solid form. This specific composition is used for increasing innate immunity in the mammal before and after the infection has occurred.

4 Claims, 2 Drawing Sheets

COMPOSITION AND ITS USE FOR INCREASING INNATE IMMUNE HEALTH

FIELD OF THE INVENTION

The subject matter disclosed in this application relates generally to the field of new composition or a nutrient mixture to be used for the improvement of innate immune health by aiding phagocytosis.

BACKGROUND

In the human body there are innate immunity and adaptive immunity. The first line of defense is innate immunity. According to Martin J. Spiering (2015) macrophages and lymphocytes sense and devour microbes, damaged cells, and other foreign materials in the body. Certain proteins in the blood (such as proteins of the complement system and those released by natural killer cells, along with antimicrobial host-defense peptides) attach to foreign organisms and toxins to initiate their destruction. Lymphocytes secrete IL-6 along with other interleukins to help NK cells.

Immunity is challenged every day in our lives due to pollution, viral and bacterial infections, seasonal infections such as flu and cancer. The first line of defense is innate immunity and adaptive innate immunity. The further the infection spreads the adaptive immunity takes over and supplemental medications are required. There is a need for boosting innate immunity proactively and subsequently after infection in a cost effective but sustained way.

SUMMARY

The present invention discloses an innate immunity building mixture or composition of various nutrients and micronutrients as a treatment to boost innate immunity. In one embodiment, a new method of proactively promoting innate immunity by preemptive intake of the said composition or mixture is disclosed. In one embodiment, the deleterious effect of pathogenic bacteria in a mammal is disclosed and treating by administering the composition or mixture is disclosed. In another embodiment, a composition being used as a pretreatment and post treatment for rectifying the damage caused by pathogens is disclosed. In another embodiment, the effect of the composition on Natural Killer (NK) cells to boost the phagocytosis and prevent cell death by immune boosting effect of the composition or mixture is disclosed. In another embodiment, a composition being used as a post treatment for rectifying the damage caused by pathogens is disclosed.

In one embodiment, the An innate immunity building composition or mixture consisting of Vitamin C, Vitamin B-complex, Vitamin E, *Aronia melanocarpa* extract, Fucoidan, Ginger extract, Zinc, Selenium, Alpha lipoic acid, White mulberry extract, Lychee fruit extract, and Sour (Tart) cherry fruit extract is disclosed. In one embodiment, the total concentration of composition in vitro is consisting of Vitamin C, Vitamin B-complex, Vitamin E, *Aronia melanocarpa* extract, Fucoidan, Ginger extract, Zinc, Selenium, Alpha lipoic acid, White mulberry extract, Lychee fruit extract, and Sour (Tart) cherry fruit extract is 75 µg/ml.

In one embodiment, An innate immunity building mixture or composition consists of natural as well as chemical nutrients and micronutrients. In one embodiment, Vitamin C, Vitamin B-complex, Vitamin E, Ginger extract, Zinc, Selenium, Alpha lipoic acid and White mulberry extract is used at 5 µg/ml concentration in vitro. In another embodiment, *Aronia melanocarpa* extract, Fucoidan and Lychee fruit extract varies between 5-20 µg/ml. In another embodiment the composition is administered as a pretreatment to enhance innate immunity in a mammal. In another embodiment the composition is administered as a posttreatment to enhance innate immunity in a mammal. In another embodiment the composition is administered as a pretreatment and posttreatment to enhance innate immunity in a mammal. In one embodiment a method of using the composition of the nutrient combination in range of 5-20 µg/ml are disclosed.

The physiological dose after calculation for mammal consumption is in the range of Vitamin C 1 mg-50, 000 g, Vitamin B-complex 2 µg to 1000 µg, Vitamin E 10 IU to 40,000 IU, *Aronia melanocarpa* extract 100 mg to 500 mg, Fucoidan 300 mg to 500 mg, Ginger extract 100 mg to 2 g, Zinc 0.1 mg to 1000 mg, Selenium 200 µg to 400 µg, Lipoic acid or interchangeably used as Alpha lipoic acid (ALA) 10 mg to 2000 mg, White mulberry extract 1 mg to 10,000 mg, Lychee fruit extract 1 mg to 10,000 mg and Sour (tart) cherry fruit extract 200 mg to 500 mg.

In one embodiment a method of administering the nutrient combination as a composition in range of Vitamin C 1 mg-50, 000 g, Vitamin B-complex 2 µg to 1000 µg, Vitamin E 10 IU to 40,000 IU, *Aronia melanocarpa* extract 100 mg to 500 mg, Fucoidan 300 mg to 500 mg, Ginger extract 100 mg to 2 g, Zinc 0.1 mg to 1000 mg, Selenium 200 µg to 400 µg, Lipoic acid (Alpha lipoic acid, ALA) 10 mg to 2000 mg, White mulberry extract 1 mg to 10,000 mg, Lychee fruit extract 1 mg to 10,000 mg, and Sour (tart) cherry fruit extract 200 mg to 500 mg for treating any infection is disclosed.

More specifically the composition or mixture of nutrients are used for modulating innate immune response using the range of Vitamin C 1 mg-50, 000 g, Vitamin B-complex 2 µg to 1000 µg, Vitamin E 10 IU to 40,000 IU, *Aronia melanocarpa* extract 100 mg to 500 mg, Fucoidan 300 mg to 500 mg, Ginger extract 100 mg to 2 g, Zinc 0.1 mg to 1000 mg, Selenium 200 µg to 400 µg, Lipoic acid (Alpha lipoic acid, ALA) 10 mg to 2000 mg, White mulberry extract 1 mg to 10,000 mg, Lychee fruit extract 1 mg to 10,000 mg, and Sour (tart) cherry fruit extract 200 mg to 500 mg. The composition of nutrients using the specific components mentioned above may be packaged in different drug formulations and administered to a mammal for proactive treatment and after the disease has manifested as a treatment method.

More specifically the composition of nutrients is used for modulating innate immune response at the NK cell level and IL-6 release using the range of Vitamin C 1 mg-50, 000 g, Vitamin B-complex 2 µg to 1000 µg, Vitamin E 10 IU to 40,000 IU, *Aronia melanocarpa* extract 100 mg to 500 mg, Fucoidan 300 mg to 500 mg, Ginger extract 100 mg to 2 gs, Zinc 0.1 mg to 1000 mg, Selenium 200 µg to 400 µg, Lipoic acid (Alpha lipoic acid, ALA) 10 mg to 2000 mg, White mulberry extract 1 mg to 10,000 mg, Lychee fruit extract 1 mg to 10,000 mg, and Sour (tart) cherry fruit extract 200 mg to 500 mg.

The nutrients in the composition may be substituted, added or subtracted from original combination and new ingredients may be added to have beneficial effect. Finally, the present invention is described further in the detailed description to further illustrate various aspects of the present invention.

BRIEF DESCRIPTION OF THE FIGURES

Example embodiments are illustrated by way of example and not limitation in the figures of the accompanying drawings, in which like references indicate similar elements and in which.

Others features of the present embodiments will be apparent from the accompanying drawings and from the detailed description that follows.

DETAILED DESCRIPTION

The following embodiments are described for illustrative purposes only with reference to the Figures. Those of skill in the art will appreciate that the following description is exemplary in nature, and that various modifications to the parameters set forth herein could be made without departing from the scope of the present invention. It is intended that the specification and examples be considered as examples only. The various embodiments are not necessarily mutually exclusive, as some embodiments can be combined with one or more other embodiments to form new embodiments. Description of the term composition and mixture are used interchangeably. All the ingredients are necessary to form this effective proactive treatment method.

According to Vivier et al. (2011) natural killer cells (NK cells) cells directly induce death of tumor cells and virus infected cells in the absence of specific immunization. They are defined as effector lymphocytes of innate immunity endowed with constitutive cytolytic functions. Spiering J. Martin (2015) states that NK cells and others are very influential in innate and adaptive immunity at the cytotoxic and cell based pathogen destruction stage when infection occurs.

Materials and Methods
Test Compounds.

The following compounds (natural and chemical nutrients for making a compound), with the purity between 90%-98% according to the manufacturer, were obtained from Sigma (St. Louis, Mo.): vitamin C, vitamins B-complex, selenium, fucoidan, lipoic acid, and ginger extract. The compounds such as vitamin E, and zinc, with the purity between 90%-98% according to the manufacturer, were purchased from Powder City (York, Pa.). Aronia melanocarpa extract, White mulberry extract, Lychee fruit extract, and Sour (tart) cherry fruit extract, with the purity between 97%-99% according to the manufacturer, were from Monterey Bay Spice (Watsonville, Calif.). All primary cells and cell lines were from ATCC (Manassas, Va.).

TABLE 1

|  | µg/ml | µg/ml | µg/ml |
| --- | --- | --- | --- |
| Vitamin C | 5 | 5 | 5 |
| Vitamin B-complex | 5 | 5 | 5 |
| Vitamin E | 5 | 5 | 5 |
| Aronia melanocarpa extract | 20 | 5 | 5 |
| Fucoidan | 5 | 15 | 5 |
| Ginger Extract | 5 | 5 | 5 |
| Zinc | 5 | 5 | 5 |
| Selenium | 5 | 5 | 5 |
| Alpha Lipoic acid | 5 | 5 | 5 |

TABLE 1-continued

Figure 1A:
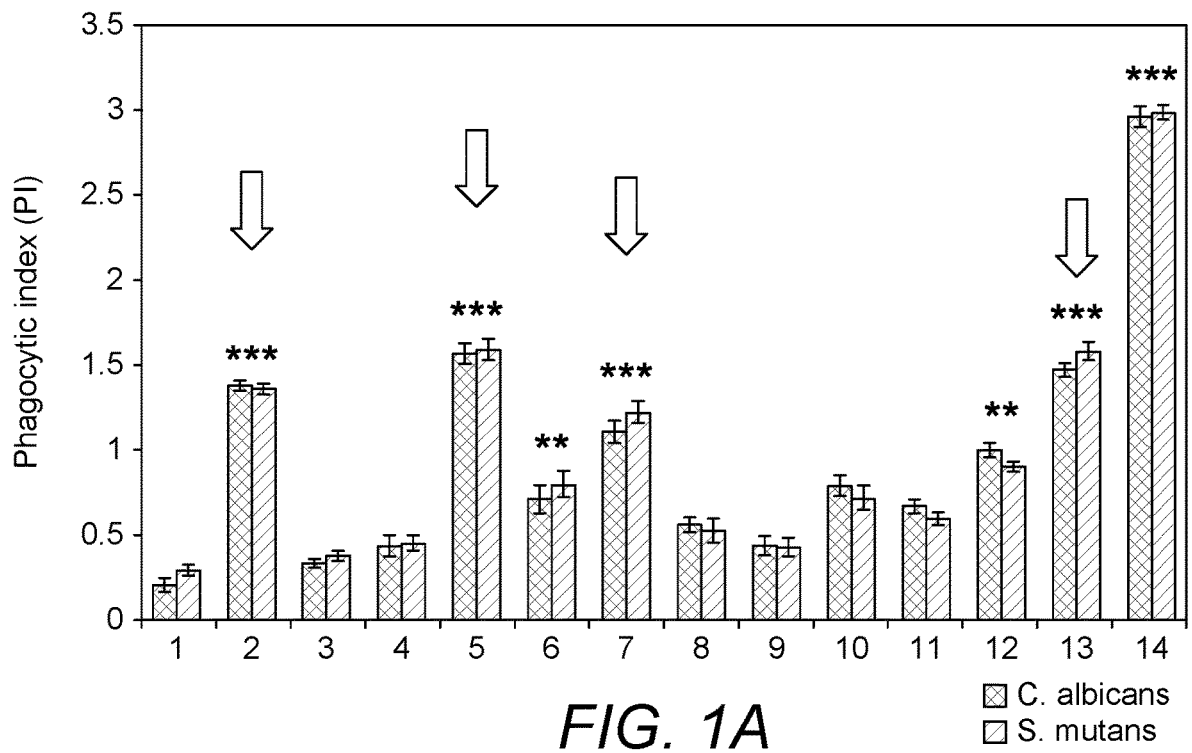
FIGS. 1A and 1B: In vitro phagocytic assay on nitroblue tetrazolium (NBT) reduction test of RAW264.7 macrophage cell line (1A) and PBMC (1B) treated with different micronutrients and plant extracts (5-20 µg/ml) for 24 h at 37° C.
Figure 1B:
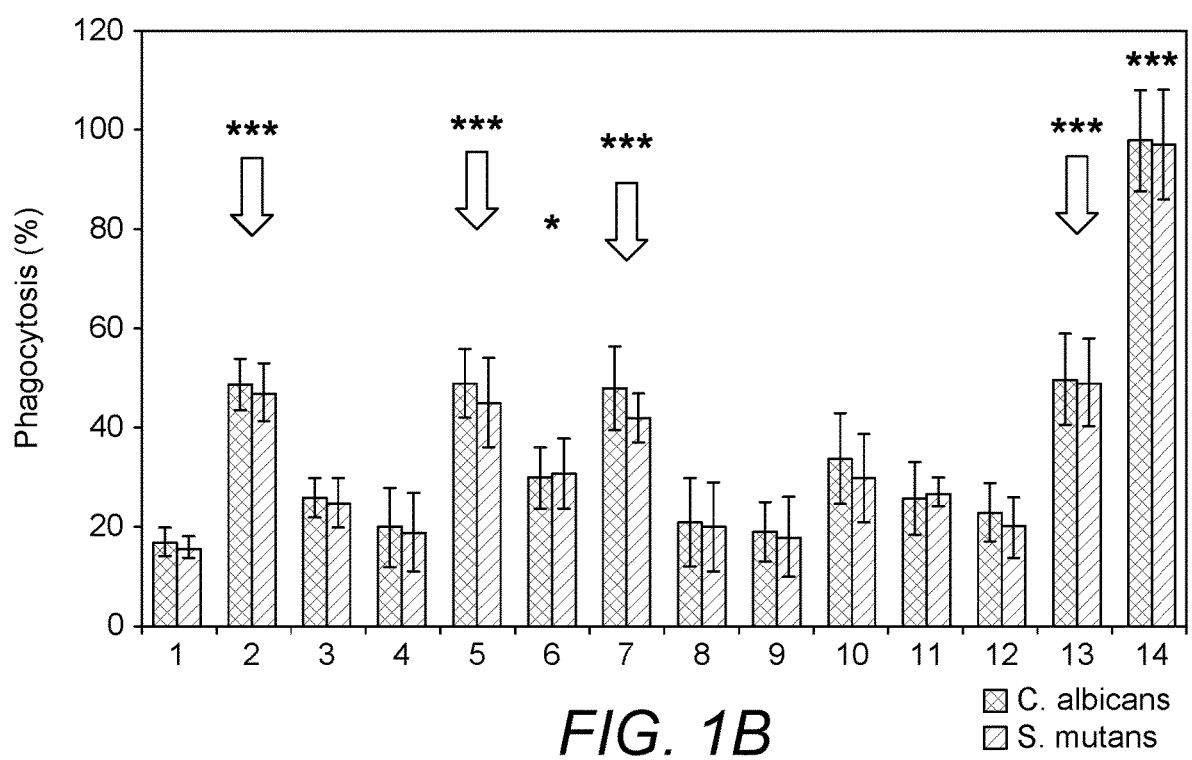
Figure 2:
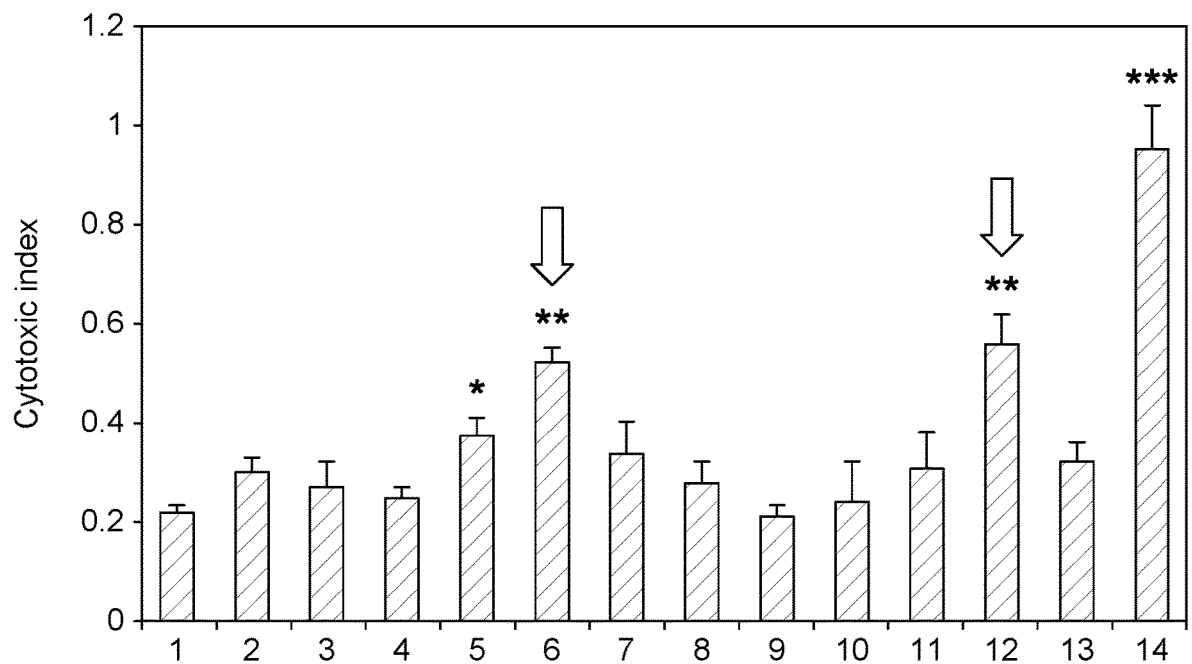
FIG. 2: Cytotoxicity of NK cells stimulated by different micronutrients and plant extracts (5-20 µg/ml) for 24 h at 37° C. toward target YAC-1 cells.
Figure 3:
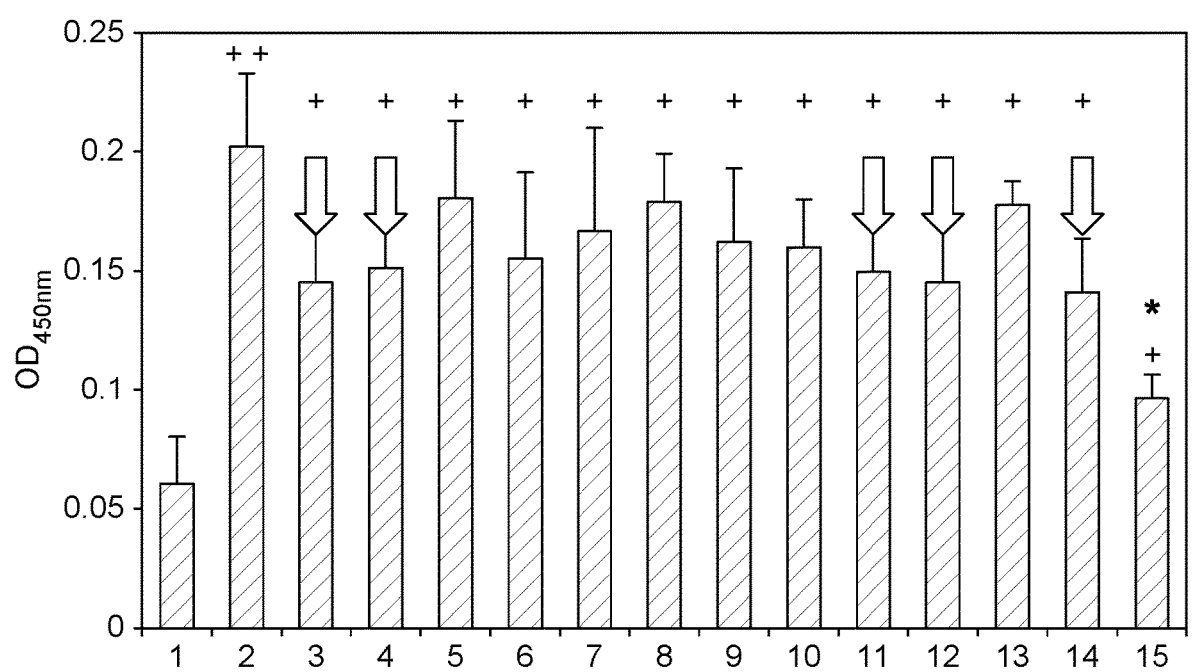
FIG. 3: The effect of naturally-derived agents on pro-inflammatory IL-6 release by RAW264.7 macrophage cell line.

|  | µg/ml | µg/ml | µg/ml |
| --- | --- | --- | --- |
| (ALA) |  |  |  |
| White mulberry extract | 5 | 5 | 5 |
| Lychee fruit extract | 5 | 10 | 5 |
| Sour cherry fruit extract | 5 | 5 | 20 |
|  | FIG. 1 = 75 µg/ml | FIG. 2 = 75 µg/ml | FIG. 3 = 75 µg/ml |

In vitro phagocytic assay (nitroblue tetrazolium (NBT) reduction test), NBT reduction assay was carried out according to the method of Rainard et al. J. Imunol. Meth. 1986; 90:197-201. RAW264.7 macrophages ($5 \times 10^6$ cells/well of a 96-well plate) were cultured with different micronutrients and plant extracts (5-20 µg/ml) for 24 h at 37° C. Thereafter, 20 µl C. albicans or S. mutans ($5 \times 10^7$ cells/ml in PBS) suspension, and 20 µl nitroblue tetrazolium (1.5 mg/ml of NBT in PBS) were added to each well. Wells that received PBS+DMSO were used as control. Next, cells were incubated for 3 h at 37° C., the supernatant was removed, and the adherent macrophages were rinsed with RPMI 1640. The cells were air dried before 80 µl of 2M KOH and 100 µl DMSO were added to each well. The absorbance was measured at 570 nm using the microplate reader. Percentage of NBT reduction (reflecting phagocytic activity) was calculated as following equation: Phagocytic Index= $(OD_{sample} - OD_{control})/OD_{control}$.

PBMC ($5 \times 10^6$ cells/well of a 96-well plate) were cultured with different micronutrients and plant extracts (5-20 µg/ml) for 24 h at 37° C. Thereafter, 20 µl S. mutans ($5 \times 10^7$ cells/ml in PBS) suspension, and 20 µl nitroblue tetrazolium (1.5 mg/ml of NBT in PBS) were added to each well. Wells that received PBS+DMSO were used as control. Next, cells were incubated for 3 h at 37° C. and the cells received 50 µl of 2M KOH and 50 µl DMSO. The absorbance was measured at 570 nm using the microplate reader. Percentage of NBT reduction (reflecting phagocytic activity) was calculated as following equation: Phagocytic Index=$(OD_{sample} - OD_{control})/OD_{control}$.

Cytotoxicity Assay of Natural Killer (NK) Cells were performed using splenic natural killer (as the effector cells) activity assay was carried out according as described by Yi et al. Carbohydr. Polym. 2012, 87:636-643. The splenocytes/splenic NK cells were plated into 96-well plates at a density of $1 \times 10^7$ cells/ml per well in a 50 µl volume, and stimulated with different micronutrients and plant extracts (5-20 µg/ml) for 24 h at 37° C. Then, YAC-1 cells ($1 \times 10^6$ cells/ml) were added into all experimental wells (group) and complete medium only was placed in the other wells as the effector control. At the same time, complete medium (100 µl), containing only YAC-1 cells ($1 \times 10^6$ cells/ml), was added into empty wells as the target control. Next, the plates were incubated for 4 h, followed by another 3 h with MTT (5 mg/ml). Then, acidified isopropyl alcohol (100 µl) was added to each well followed by 1 h incubation. The absorbance was measured at 570 nm using a microplate reader. Cytotoxicity of NK cell was expressed as Cytotoxic Index (percent lysis of target cells): $CI=[ODT-(OD_{exp.}-ODE)]/ODT \times 100$], where ODT represents OD value of the target control, whereas $OD_{exp.}$ and ODE represent OD value of the experimental group and effector control, respectively.

Phagocytosis of Live Candida albicans:

Phagocytosis assay was carried out according to the protocol of Ortega et al. Eur. J. Appl. Physiol. 1993, 66:60-64.

Preparation of *Candida albicans* suspension: The *C. albicans* culture was incubated in Sabouraud broth overnight and then centrifuged. Supernatant was discarded and the cell button was washed with sterile HBSS and centrifuged again. This step was repeated 3-4 times. The final cell button was mixed with a mixture of sterile HBSS and human serum in the proportion of 4:1. The cell suspension of concentration $1 \times 10^5$/ml was used for the experiment.

Phagocytosis evaluation. 50 µl of different micronutrients and plant extracts (5-20 µg/ml) were taken in separate Eppendorf tubes and 100 µl of HBSS, 100 µl of *C. albicans* suspension and 100 µl of PBMC suspension ($2 \times 10^6$/ml) were added to each tube. A control was the tubes that did not receive a treatment with tested agents. All the tubes were shaken gently, incubated at 37° C. for 30 min. and centrifuged at 200 g for 5 min. The supernatant was removed leaving a small droplet into which sediment was re-suspended. Smears were made, air-dried and stained with Giemsa stain. 100 PBMC were observed under a microscope, a number of ingested *C. albicans* by each cell was counted, and mean particle number (MPN) associated with each PBMC cells was calculated.

Pro-Inflammatory IL-6 Release Status:

The pro-inflammatory IL-6 release by RAW264.7 macrophages was assessed using the IL-6 Quantikine ELISA assay kit (R&D, Minneapolis, Minn.) according to the manufacturer's protocol. Briefly, $2 \times 10^6$ of cells were plated in 6-well plates and allowed to settle for 2-4 h, followed by incubation with different micronutrients and plant extracts (5-20 µg/ml) 24 h at 37° C. in 5% $CO_2$ atmosphere. After the incubation period, cells were stimulated with LPS (10 ng/ml) for additional 24 h and all supernatants were collected and subjected to ELISA assay according to manufacturer's protocol. As a positive control, LPS-stimulated cells without treatment were used. All experiments were done in triplicate.

Statistical Analysis.

Means and standard deviations were determined for all experiments and Student's t test analysis was used to determine significant differences. Statistical analysis was performed by two-sample paired t-test using GraphPad statistical software.

FIGS. 1A and 1B.

The effects of test compounds and their mixed composition on In vitro phagocytic activity and phagocytosis by RAW264.7 macrophage cell line (FIG. 1A) and PBMC (FIG. 1B). The assay used nitroblue tetrazolium (NBT) reduction test after treatment with different individual micronutrients and plant extracts (5-20 µg/ml) and their combination for 24 h at 37° C. PI and phagocytosis was tested using *C. albicans* and *S. mutants*. Values shown are mean±standard deviation (n=4). Value significantly different from corresponding control at *p<0.05, p<0.01, *p<0.001. The individual ingredients represented by numbers in the bars are:

TABLE 2

| FIG. 1A and 1B list of nutrients and mix represented in the bar. |
|---|
| 1. Control |
| 2. Vitamin C |
| 3. Vitamin B-complex |
| 4. Vitamin E |
| 5. *Aronia melanocarpa* extract |
| 6. Fucoidan |
| 7. Ginger extract |

TABLE 2-continued

| FIG. 1A and 1B list of nutrients and mix represented in the bar. |
|---|
| 8. Zinc |
| 9. Selenium |
| 10. Alpha lipoic acid |
| 11. White mulberry extract |
| 12. Litchi fruit extract |
| 13. Sour cherry fruit extract |
| 14. Mixture or composition |

Summary:

The composition of 12 naturally and chemical occurring ingredients was more effective than any of its individual compound in stimulating phagocytic activity of RAW264.7 macrophages. The mixture was 12 times more effective than control and at least two fold more effective when compared to the most effective individual agents that were: Vitamin C, *Aronia melanocarpa* extract, Ginger extract, and Sour cherry fruit extract. The phagocytosis of *C. albicans* and *S. mutans* by human PBMC treated with the mixture of 12 test components as composition was 100%. While the most effective individual compounds: vitamin C, *Aronia melanocarpa* extract, Ginger extract and Sour cherry fruit extract could stimulate phagocytosis only by up to 50%.

FIG. 2.

Cytotoxicity of NK cells toward target YAC-1 cells in the presence of different micronutrients and plant extracts (5-20 µg/ml) used individually and in a combination for 24 h at 37° C. Cytotoxicity of NK cells was assessed by the MTT assay and expressed as the mean±standard deviation (n=4). Value significantly different from corresponding control at *p<0.05, p<0.01, *p<0.001.

TABLE 3

| FIG. 2 list of nutrients and mix represented in the bar. |
|---|
| 1. Control |
| 2. Vitamin C |
| 3. Vitamin B-complex |
| 4. Vitamin E |
| 5. *Aronia melanocarpa* extract |
| 6. Fucoidan |
| 7. Ginger extract |
| 8. Zinc |
| 9. Selenium |
| 10. Alpha lipoic acid |
| 11. White mulberry extract |
| 12. Litchi fruit extract |
| 13. Sour cherry fruit extract |
| 14. Mixture or composition |

Summary:

Cytotoxic potency of human NK cells treated with the composition of 12 naturally occurring substances was about 80% higher than a control and about 50% higher than the two most effective individual compounds: fucoidan or Litchi fruit extract. This clearly shows that innate immunity plays a key role and gets boost from the said composition to enhance the innate immunity and reduce the inflammation.

FIG. 3.

The effect of naturally-derived agents and their mixture on release of pro-inflammatory IL-6 by RAW264.7 macrophage cell line. Macrophages were pre-incubated with different micronutrients and plant extracts (5-20 µg/ml) individually and in a mixture followed by their stimulation with Lipopolysaccharide (LPS). Each column represents the mean±standard deviation (n=4). Value significantly different at *p<0.05, compared to control with LPS, +p<0.05 compared to control w/o LPS, ++p<0.001 compared to control w/o LPS.

TABLE 2

FIG. 3 list of nutrients and mix represented in the bar.

1. Control w/o LPS
2. Control with LPS
3. Vitamin C
4. Vitamin B-complex
5. Vitamin E
6. *Aronia melanocarpa* extract
7. Fucoidan
8. Ginger extract
9. Zinc
10. Selenium
11. Alpha Lipoic acid
12. White mulberry extract
13. Litchi fruit extract
14. Sour cherry fruit extract
15. Mixture or composition Summary:

The mixture or composition of 12 naturally and chemically derived ingredients had a strong 50% inhibitory effect on IL6 secretion by LPS stimulated RAW264.7 cells. Exposure of these macrophages to LPS resulted in over 300% stimulation of IL-6 secretion, while the Mix, could alleviate these effects to the level of IL-6 secretion which was only 40% higher than observed without LPS exposure. The composition was significantly more effective than the best natural compounds: Vitamin C, vitamin B-complex, Lipoic acid, White mulberry, and Sour cherry fruit extract. The mix of all 12 ingredients as a composition was significantly more effective than its individual compounds in various aspects of immunity, such as: enhancing phagocytic activity and ability of splenocytes in eliminating live bacteria, enhancing activity of NK cells and decreasing IL-6 secretion.

The physiological dose of the composition of nutrients after calculation for mammal consumption is in the range of Vitamin C 1 mg to 50,000 g, Vitamin B-complex 2 μg to 1000 μg, Vitamin E 10 IU to 40,000 IU, *Aronia melanocarpa* extract 100 mg to 500 mg, Fucoidan 300 mg to 500 mg, Ginger extract 100 mg to 2 g, Zinc 0.1 mg to 1000 mg, Selenium 200 μg to 400 μg, Lipoic acid (Alpha lipoic acid, ALA) 10 mg to 2000 mg, White mulberry extract 1 mg to 10,000 mg, Lychee fruit extract-1 mg to 10,000 mg and Sour (tart) cherry fruit extract 200 mg to 500 mg.

Every drug formulation and mode of delivery for a mammal has the composition containing The physiological dose after calculation for mammal consumption is in the range of Vitamin C 1 mg-50, 000 g, Vitamin B-complex 2 μg to 1000 μg, Vitamin E 10 IU to 40,000 IU, *Aronia melanocarpa* extract 100 mg to 500 mg, Fucoidan 300 mg to 500 mg, Ginger extract 100 mg to 2 g, Zinc 0.1 mg to 1000 mg, Selenium 200 μg to 400 μg, Lipoic acid (Alpha lipoic acid, ALA) 10 mg to 2000 mg, White mulberry extract 1 mg to 10,000 mg, Lychee fruit extract 1 mg to 10,000 mg, and Sour (tart) cherry fruit extract 200 mg to 500 mg with other necessary additives and fillers in the dosage form. Drug formulations suitable for these administration routes can be produced by adding one or more pharmacologically acceptable carriers to the agent and then treating the mixture through a routine process known to those skilled in the art. The mode of administration includes, but not limited to, are non-invasive peroral, topical (example transdermal), enteral, transmucosal, targeted delivery, sustained release delivery, delayed release, pulsed release and parenteral methods. Peroral administration may be administered both in liquid and dry state.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition as an active ingredient. Subject compositions may also be administered as a bolus, electuary, or paste.

When an oral solid drug product is prepared, nutrient mixture is mixed with an excipient (and, if necessary, one or more additives such as a binder, a disintegrant, a lubricant, a coloring agent, a sweetening agent, and a flavoring agent), and the resultant mixture is processed through a routine method, to thereby produce an oral solid drug product such as tablets, coated tablets, granules, powder, or capsules. Additives may be those generally employed in the art. Examples of the excipient include lactate, sucrose, sodium chloride, glucose, starch, calcium carbonate, kaolin, microcrystalline cellulose, and silicic acid; examples of the binder include water, ethanol, propanol, simple syrup, glucose solution, starch solution, liquefied gelatin, carboxymethylcellulose, hydroxypropylcellulose, hydroxypropyl starch, methyl cellulose, ethyl cellulose, shellac, calcium phosphate, and polyvinyl pyrrolidone; examples of the disintegrant include dried starch, sodium arginate, powdered agar, sodium hydrogencarbonate, calcium carbonate, sodium lauryl sulfate, monoglyceryl stearate, and lactose; examples of the lubricant include purified talc, stearic acid salts, borax, and polyethylene glycol; and examples of the sweetening agent include sucrose, orange peel, citric acid, and tartaric acid.

When a liquid drug product for oral administration is prepared, nutrient mixture is mixed with an additive such as a sweetening agent, a buffer, a stabilizer, or a flavoring agent, and the resultant mixture is processed through a routine method, to thereby produce an orally administered liquid drug product such as an internal solution medicine, syrup, or elixir. Examples of the sweetening agent include vanillin; examples of the buffer include sodium citrate; and examples of the stabilizer include tragacanth, acacia, and gelatin.

For purposes of transdermal (e.g., topical) administration, dilute sterile, aqueous or partially aqueous solutions (usually in about 0.1% to 5% concentration), otherwise similar to the above parenteral solutions, may be prepared.

Formulations for rectal or vaginal administration may be presented as a suppository, which may be prepared by mixing a subject composition with one or more suitable non-irritating carriers comprising, for example, cocoa butter, polyethylene glycol, a suppository wax, or a salicylate, and which is solid at room temperature, but liquid at body temperature and, therefore, will melt in the appropriate body cavity and release the encapsulated compound(s) and composition(s). Formulations which are suitable for vaginal administration also include pessaries, tampons, creams, gels, pastes, foams, or spray formulations containing such carriers as are known in the art to be appropriate.

A targeted release portion can be added to the extended release system by means of either applying an immediate release layer on top of the extended release core; using coating or compression processes or in a multiple unit system such as a capsule containing extended and immediate release beads.

When used with respect to a pharmaceutical composition or other material, the term "sustained release" is art-recognized. For example, a therapeutic composition which releases a substance over time may exhibit sustained release characteristics, in contrast to a bolus type administration in which the entire amount of the substance is made biologically available at one time. For example, in particular embodiments, upon contact with body fluids including blood, spinal fluid, mucus secretions, lymph or the like, one or more of the pharmaceutically acceptable excipients may undergo gradual or delayed degradation (e.g., through hydrolysis) with concomitant release of any material incorporated therein, e.g., an therapeutic and/or biologically active salt and/or composition, for a sustained or extended period (as compared to the release from a bolus). This release may result in prolonged delivery of therapeutically effective amounts of any of the therapeutic agents disclosed herein.

Current efforts in the area of drug delivery include the development of targeted delivery in which the drug is only active in the target area of the body (for example, in cancerous tissues) and sustained release formulations in which the drug is released over a period of time in a controlled manner from a formulation. Types of sustained release formulations include liposomes, drug loaded biodegradable microspheres and drug polymer conjugates.

Delayed release dosage formulations are created by coating a solid dosage form with a film of a polymer which is insoluble in the acid environment of the stomach, but soluble in the neutral environment of the small intestines. The delayed release dosage units can be prepared, for example, by coating a drug or a drug-containing composition with a selected coating material. The drug-containing composition may be a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Alternatively, a delayed release tablet may be formulated by dispersing tire drug within a matrix of a suitable material such as a hydrophilic polymer or a fatty compound. Suitable hydrophilic polymers include, but are not limited to, polymers or copolymers of cellulose, cellulose ester, acrylic acid, methacrylic acid, methyl acrylate, ethyl acrylate, and vinyl or enzymatically degradable polymers or copolymers as described above. These hydrophilic polymers are particularly useful for providing a delayed release matrix. Fatty compounds for use as a matrix material include, but are not limited to, waxes (e.g. carnauba wax) and glycerol tristearate. Once the active ingredient is mixed with the matrix material, the mixture can be compressed into tablets.

A pulsed release-dosage is one that mimics a multiple dosing profile without repeated dosing and typically allows at least a twofold reduction in dosing frequency as compared to the drug presented as a conventional dosage form (e.g., as a solution or prompt drug-releasing, conventional solid dosage form). A pulsed release profile is characterized by a time period of no release (lag time) or reduced release followed by rapid drug release.

The phrases "parenteral administration" and "administered parenterally" as used herein refer to modes of administration other than enteral and topical administration, such as injections, and include without limitation intravenous, intramuscular, intrapleural, intravascular, intrapericardial, intra-arterial, intrathecal, intracapsular, intraorbital, intracardiac, intradennal, intraperitoneal, transtracheal, subcutaneous, subcuticular, intra-articular, subcapsular, subarachnoid, intraspinal and intrastemal injection and infusion.

Certain pharmaceutical compositions disclosed herein suitable for parenteral administration comprise one or more subject compositions in combination with one or more pharmaceutically acceptable sterile, isotonic, aqueous, or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic within the blood of the intended recipient or suspending or thickening agents.

When an injection product is prepared, nutrient mixture is mixed with an additive such as a pH regulator, a buffer, a stabilizer, an isotonicity agent, or a local anesthetic, and the resultant mixture is processed through a routine method, to thereby produce an injection for subcutaneous injection, intramuscular injection, or intravenous injection. Examples of the pH regulator or buffer include sodium citrate, sodium acetate, and sodium phosphate; examples of the stabilizer include sodium pyrosulfite, EDTA, thioglycollic acid, and thiolactic acid; examples of the local anesthetic include procaine hydrochloride and lidocaine hydrochloride; and examples of the isotonicity agent include sodium chloride and glucose.

The phrase "pharmaceutically acceptable" is art-recognized. In certain embodiments, the term includes compositions, polymers and other materials and/or dosage forms which are within the scope of sound medical judgment, suitable for use in contact with the tissues of mammals, human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the pharmaceutical compositions described herein are formulated in a manner such that said compositions will be delivered to a mammal in a therapeutically effective amount, as part of a prophylactic, preventive or therapeutic treatment.

In certain embodiments, the dosage of the nutrient mixture compositions, which may be referred as therapeutic composition provided herein may be determined by reference to the plasma concentrations of the therapeutic composition or other encapsulated materials.

The therapeutic compositions provided by this application may be administered to a subject in need of treatment by a variety of conventional routes of administration, including orally, topically, parenterally, e.g., intravenously, subcutaneously or intramedullary. Further, the therapeutic compositions may be administered intranasally, as a rectal suppository, or using a "flash" formulation, i.e., allowing the medication to dissolve in the mouth without the need to use water. Furthermore, the compositions may be administered to a subject in need of treatment by controlled release dosage forms, site specific drug delivery, transdermal drug delivery, patch (active/passive) mediated drug delivery, by stereotactic injection, or in nanoparticles.

Expressed in terms of concentration, an active ingredient can be present in the therapeutic compositions of the present invention for localized use about the cutis, intranasally, pharyngolaryngeally, bronchially, intravaginally, rectally, or ocularly.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The most common routes of administration also include the preferred transmucosal (nasal, buccal/sublingual, vaginal, ocular and rectal) and inhalation routes.

In addition, in certain embodiments, subject compositions of the present application maybe lyophilized or subjected to another appropriate drying technique such as spray drying. The subject compositions may be administered once, or may be divided into a number of smaller doses to be administered at varying intervals of time, depending in part on the release rate of the compositions and the desired dosage.

Formulations useful in the methods provided herein include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject composition which may be combined with a carrier material to produce a single dose may vary depending upon the subject being treated, and the particular mode of administration.

The therapeutically acceptable amount described herein may be administered in inhalant or aerosol formulations. The inhalant or aerosol formulations may comprise one or more agents, such as adjuvants, diagnostic agents, imaging agents, or therapeutic agents useful in inhalation therapy. The final aerosol formulation may for example contain 0.005-90% w/w, for instance 0.005-50%, 0.005-5% w/w, or 0.01-1.0% w/w, of medicament relative to the total weight of the formulation.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants. The therapeutic acceptable dosage of the nutrient mixture may be combined with other drugs and may be treated as a combination drug.

What is claimed is:

1. An innate immunity building nutrient mixture, consisting of: a Vitamin C, Vitamin B-complex, Vitamin E, *Aronia melanocarpa* extract, Fucoidan, Ginger extract, Zinc, Selenium, Alpha lipoic acid, White mulberry extract, Lychee fruit extract and Sour cherry fruit extract, wherein the physiological dose of the composition of above nutrients after calculation for mammal consumption ranges in an amount as follows; Vitamin C 1 from mg to 50,000 g, Vitamin B-complex from 2 µg to 1000 µg, Vitamin E from 10 IU to 40,000 IU, *Aronia melanocarpa* extract from 100 mg to 500 mg, Fucoidan from 300 mg to 500 mg, Ginger extract from 100 mg to 2 g, Zinc from 0.1 mg to 1000 mg, Selenium from 200 µg to 400 µg, Alpha lipoic Acid from 10 mg to 2000 mg, White mulberry extract from 1 mg to 10000 mg, Lychee fruit extract from 1 mg to 10000 mg, and Sour cherry fruit extract from 200 mg to 500 mg.

2. The composition of claim 1, wherein the composition is administered to a mammal for increasing innate immunity.

3. A nutrient mixture composition consisting of: a Vitamin C, Vitamin B-complex, Vitamin E, *Aronia melanocarpa* extract, Fucoidan, Ginger extract, Zinc, Selenium, Alpha lipoic acid, White mulberry extract, Lychee fruit extract and Sour cherry fruit extract to increase innate immunity in a mammal treated before and after the bacterial infection, wherein the physiological dose of the composition of above nutrients after calculation for mammal consumption ranges in an amount as follows; Vitamin C 1 from mg to 50,000 g, Vitamin B-complex from 2 µg to 1000 µg, Vitamin E from 10 IU to 40,000 IU, *Aronia melanocarpa* extract from 100 mg to 500 mg, Fucoidan from 300 mg to 500 mg, Ginger extract from 100 mg to 2 g, Zinc from 0.1 mg to 1000 mg, Selenium from 200 µg to 400 µg, Alpha lipoic Acid from 10 mg to 2000 mg, White mulberry extract from 1 mg to 10000 mg, Lychee fruit extract from 1 mg to 10000 mg, and Sour cherry fruit extract from 200 mg to 500 mg.

4. A method of increasing an innate immunity to fight bacterial infections in a mammal, by administering to the mammal a composition consisting of: a Vitamin C, Vitamin B-complex, Vitamin E, *Aronia melanocarpa* extract, Fucoidan, Ginger extract, Zinc, Selenium, Alpha lipoic acid, White mulberry extract, Lychee fruit extract and Sour cherry fruit extract, wherein the physiological dose of the composition of above nutrients after calculation for mammal consumption ranges in an amount as follows; Vitamin C 1 from mg to 50,000 g, Vitamin B-complex from 2 µg to 1000 µg, Vitamin E from 10 IU to 40,000 IU, *Aronia melanocarpa* extract from 100 mg to 500 mg, Fucoidan from 300 mg to 500 mg, Ginger extract from 100 mg to 2 g, Zinc from 0.1 mg to 1000 mg, Selenium from 200 µg to 400 µg, Alpha lipoic Acid from 10 mg to 2000 mg, White mulberry extract from 1 mg to 10000 mg, Lychee fruit extract from 1 mg to 10000 mg, and Sour cherry fruit extract from 200 mg to 500 mg.

\* \* \* \* \*